United States Patent
Heitsch et al.

(10) Patent No.: US 6,429,222 B2
(45) Date of Patent: Aug. 6, 2002

(54) 1-(P-THIENYLBENZYL)IMIDAZOLES AS AGONISTS OF ANGIOTENSIN (1-7) RECEPTORS, PROCESSES FOR THEIR PREPARATION, THEIR USE, AND PHARMACEUTICAL PREPARATIONS COMPRISING THEM

(76) Inventors: Holger Heitsch, Mainz-Kastel; Gabriele Wiemer, Kronberg, both of (DE)

( * ) Notice: Subject to any disclaimer, the term of this patent is extended or adjusted under 35 U.S.C. 154(b) by 0 days.

(21) Appl. No.: 09/809,008

(22) Filed: Mar. 16, 2001

Related U.S. Application Data

(62) Division of application No. 09/564,544, filed on May 4, 2000, now Pat. No. 6,235,766.

(30) Foreign Application Priority Data

May 5, 1999 (DE) .......................... 199 20 815
Dec. 21, 1999 (DE) .......................... 199 61 686

(51) Int. Cl.$^7$ ................. C07D 233/64; A61K 31/4178; A61P 9/00
(52) U.S. Cl. ..................... 514/397; 548/315.1
(58) Field of Search ................. 514/397; 548/315.1

(56) References Cited

U.S. PATENT DOCUMENTS 5,198,438 A * 3/1993 Allen et al. ............... 514/235

* cited by examiner

Primary Examiner—Robert W. Ramsuer
Assistant Examiner—Andrea D'Souza-Small

(57) ABSTRACT

The invention relates to novel 1-(p-thienylbenzy)imidazoles of formula (I)

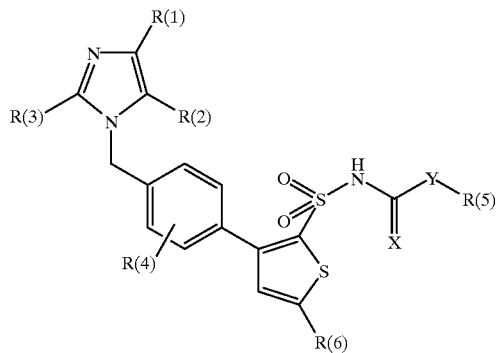

where the radicals R(1) to R(6), X, and Y have the meaning indicated in the description, which are potent agonists of angiotensin (1–7) receptors and owing to the production and release of the vasorelaxant, antithrombotic, and cardioprotective messengers cyclic 3',5'-guanosine monophosphate (cGMP) and nitrogen monoxide (NO) associated with the stimulation of these receptors on endothelial cells are valuable pharmaceuticals for the treatment and prophylaxis of high blood pressure, cardiac hypertrophy, cardiac insufficiency, coronary heart diseases such as angina pectoris, cardiac infarct, vascular restenosis after angioplasty, cardiomyopathies, endothelial dysfunction or endothelial damage, e.g., as a result of arteriosclerotic processes or diabetes mellitus, and also of arterial and venous thromboses.

5 Claims, No Drawings

1-(P-THIENYLBENZYL)IMIDAZOLES AS AGONISTS OF ANGIOTENSIN (1-7) RECEPTORS, PROCESSES FOR THEIR PREPARATION, THEIR USE, AND PHARMACEUTICAL PREPARATIONS COMPRISING THEM

This application is a divisional of U.S. Ser. No. 09/564,544, filed May 4, 2000, U.S. Pat. No. 6,235,706 filed May 22, 2001.

The invention relates to novel 1-(p-thienylbenzyl) imidazoles of formula (I),

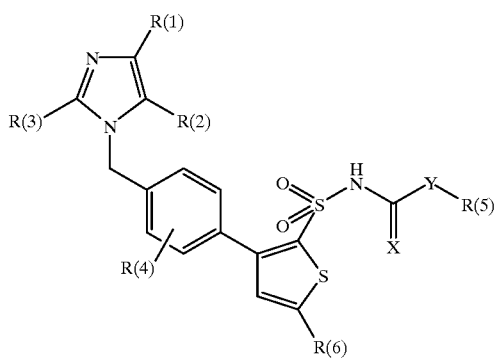

which are potent agonists of angiotensin (1–7) receptors and, because of the production land release of the vasorelaxant, antithrombotic, and cardio-protective messengers cyclic 3',5'-guanosine monophosphate (cGMP) and nitrogen monoxide (NO) associated with the stimulation of these receptors on endothelial cells, are valuable pharmaceuticals for the treatment and prophylaxis of high blood pressure, cardiac hypertrophy, cardiac insufficiency, coronary heart diseases such as angina pectoris, cardiac infarct, vascular restenosis after angioplasty, cardiomyopathies, an endothelial dysfunction or endothelial damage, e.g., as a result of arteriosclerotic processes or in diabetes mellitus, and of arterial and venous thrombosis.

EP-A 512675 and WO 94/27597 describe thienylbenzyl-substituted imidazoles as angiotensin II receptor-antagonists and their use for the treatment of hypertension, cardiac insufficiency, migraine, Alzheimer's disease, and as antidepressants. Moreover, thienylbenzyl-substituted imidazopyridines are disclosed in EP-A 513979 as antagonists of angiotensin II receptors and their use for the treatment of hypertension, cardiac insufficiency, migraine, and Alzheimer's disease, and in U.S. Pat. No. 5,444,067 as angiotensin II agonists and their use for the treatment of hypotension and of hypoaldosteronism. In addition, in EP-A 534706 thienylbenzyl-substituted quinazolinones and pyridopyrimidones and in EP-A 510812 thienylbenzyl-substituted triazoles are disclosed as antagonists of angiotensin II receptors.

The 1-(p-thienylbenzyl)imidazoles of formula (I) described here and their use as agonists of angiotensin (1–7) receptors are in this case neither described, anticipated, nor suggested in the applications mentioned.

Surprisingly, it has been found that 1-(p-thienylbenzyl) imidazoles of formula (I) have a marked action on angiotensin (1–7) receptors and mimic the biological action of the effector hormone angiotensin (1–7).

The invention thus relates to compounds of formula (I)

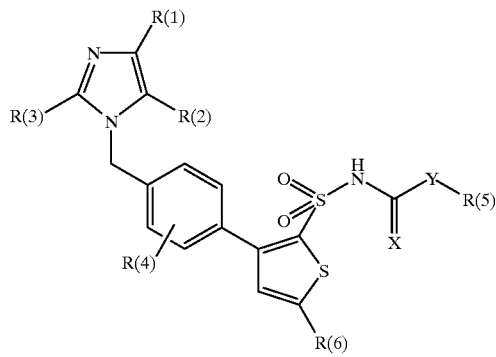

in which:
R(1) is
  (1) halogen;
  (2) hydroxyl;
  (3) (C$_1$–C$_4$)-alkoxy;
  (4) (C$_1$–C$_8$)-alkoxy, wherein 1 to 6 carbon atoms are replaced by the heteroatoms O, S, or NH, preferably by O;
  (5) (C$_1$–C$_4$)-alkoxy, substituted by a saturated cyclic ether such as tetrahydropyran or tetrahydrofuran;
  (6) O—(C$_1$–C$_4$)-alkenyl;
  (7) O—(C$_1$–C$_4$)-alkylaryl; or
  (8) aryloxy, unsubstituted or substituted by a substituent selected from halogen, (C$_1$–C$_3$)-alkyl, (C$_1$–C$_3$)-alkoxy, and trifluoromethyl;
R(2) is
  (1) CHO;
  (2) COOH; or
  (3) CO—O—(C$_1$–C$_4$)-alkyl;
R(3) is
  (1) (C$_1$–C$_4$)-alkyl; or
  (2) aryl;
R(4) is
  (1) hydrogen;
  (2) halogen; or
  (3) (C$_1$–C$_4$)-alkyl;
X is
  (1) oxygen; or
  (2) sulfur;
Y is
  (1) oxygen; or
  (2) —NH—;
R(5) is
  (1) hydrogen;
  (2) (C$_1$–C$_6$)-alkyl; or
  (3) (C$_1$–C$_4$)-alkylaryl;
  where R(5) can only be hydrogen if Y has the meaning mentioned under (2); and
R(6)
  (1) (C$_1$–C$_5$)-alkyl;
in any stereoisomeric form or mixture thereof in any ratio, or a physiologically tolerable salt thereof;
wherein R(1) may not be halogen when R(2) is COOH or CO—O—(C$_1$–C$_4$)-alkyl.

The term alkyl means, if not stated otherwise, straight-chain or branched saturated hydrocarbon radicals. This also applies to substituents derived therefrom such as alkoxy or the radical S(O)m-alkyl. Examples of alkyl radicals are methyl, ethyl, n-propyl, isopropyl, isobutyl, sec-butyl, tert-butyl, n-pentyl, and n-hexyl. Examples of alkoxy are methoxy, ethoxy, n-propoxy, and isopropoxy. Examples of aryloxy are phenoxy or naphthoxy. Phenoxy is preferred.

Alkenyl represents mono- or polyunsaturated hydrocarbon radicals in which the double bonds can be situated in any desired positions. Examples of alkenyl are vinyl, prompenyl, and butenyl.

Halogen represents fluorine, chlorine, bromine, or iodine, preferably chlorine or fluorine.

Aryl represents phenyl or naphthyl, preferably phenyl.

In substituted aryl radicals, the subsfituents can be situated in any desired position relative to one another.

Examples of arylalkyl radicals are phenylmethyl (benzyl), phenylethyl, phenylpropyl, phenylbutyl, naphthylmethyl, naphthylethyl, naphthylpropyl, and naphthylbutyl.

If compounds of formula (I) contain one or more acidic or basic groups, the invention also encompasses the corresponding physiologically tolerable salts, in particular the pharmaceutically utilizable salts. Thus, compounds of formula (I) which carry acidic groups, such as one or more COOH groups, can be present, for example, as their alkali metal salts, preferably sodium or potassium salts, or as their alkaline earth metal salts, e.g., calcium or magnesium salts, or as ammonium salts, e.g., as salts with ammonia or organic amines or amino acids. Compounds of formula (I) which carry one or more basic, i.e., protonatable, groups, can also be used in the form of their physiologically tolerable acid addition salts with inorganic or organic acids, for example as hydrochlorides, phosphates, sulfates, methanesulfonates, acetates, lactates, maleates, fumarates, malates, or gluconates. If compounds of formula (I) simultaneously contain acidic and basic groups in the molecule, the invention also includes, in addition to the salt forms outlined, internal salts, so-called betaines. Salts can be obtained from compounds of formula (I) by customary processes, for example by combination with an acid or base in a solvent or dispersant or otherwise from other salts by anion exchange.

Physiologically tolerable salts of compounds of formula (I) are to be understood, for example, as also meaning organic and inorganic salts, such as are described in *Remington's Pharmaceutical Sciences* (17$^{th}$ Edition (1985) 1418). On account of the physical and chemical stability and the solubility, preferred acidic groups are, inter alia, sodium, potassium, calcium, and ammonium salts; preferred basic groups are, inter alia, salts of hydrochloric acid, sulfuric acid, phosphoric acid, or of carboxylic acids or sulfonic acids, such as, for example, acetic acid, citric acid, benzoic acid, maleic acid, fumaric acid, tartaric acid, and p-toluenesulfonic acid.

The present invention furthermore comprises solvates of compounds of formula (I), for example hydrates or adducts with alcohols, and also derivatives of compounds of formula (I) such as, for example, esters, and prodrugs and active metabolites.

Preferred compounds of formula (I) are those in which

R(1) is
(1) chlorine;
(2) hydroxyl;
(3) methoxy, ethoxy, or propyloxy;
(4) methoxyethoxy or methoxypropoxy;
(5) allyloxy; or
(6) phenoxy;

R(4) is
(1) hydrogen; or
(2) chlorine;

R(5) is
(1) hydrogen; or
(2) $(C_1–C_4)$-alkyl;

R(6) is
(1) n-propyl or 2-isobutyl;

and the other radicals are as defined above, in any stereoisomeric form or mixture thereof in any ratio, or a physiologically tolerable salt thereof.

Compounds of formula (I) are furthermore preferred in which

R(1) is
halogen, preferably chlorine, $(C_1–C_4)$-alkoxy, preferably methoxy, ethoxy, or propyloxy, particularly preferably methoxy, or $(C_1–C_8)$-alkoxy, where 1 to 6 carbon atoms are replaced by the heteroatoms O, S, or NH, preferably O, preferably methoxyethoxy or methoxypropoxy;

R(2) is
CHO;

R(3) is
aryl, preferably phenyl;

R(4) is
halogen, preferably chlorine, or hydrogen;

R(5) is
$(C_1–C_6)$-alkyl, preferably methyl, ethyl, propyl, or butyl;

R(6) is
$(C_1–C_5)$-alkyl, preferably ethyl, propyl, or butyl;

X is
oxygen;

Y is
oxygen or —NH—;

in any stereoisomeric form or mixture thereof in any ratio, or a physiologically tolerable salt thereof.

Compounds of formula (I) are very particularly preferred when these are compounds of formula (II)

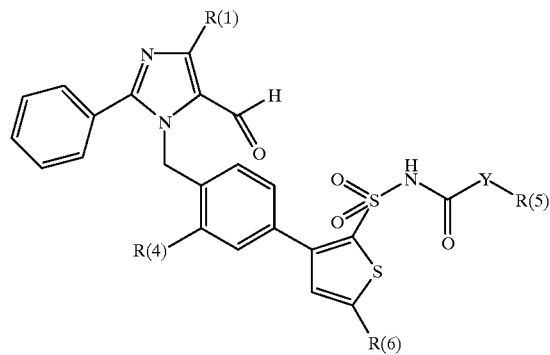

(II)

in which the radicals R(1), R(4), R(5), R(6), and Y have the abovementioned meaning, in any stereoisomeric form or mixture thereof in any ratio, or a physiologically tolerable salt thereof.

Preferred compounds of formula (I) are also those in which R(1) is $(C_1–C_4)$-alkoxy or $(C_1–C_8)$-alkoxy, where 1 to 6 carbon atoms are replaced by the heteroatoms O, S, or NH, preferably O, and the other radicals are as defined above, in any stereoisomeric form or mixture thereof in any ratio, or a physiologically tolerable salt thereof.

Particularly preferred compounds of formula (I) are also those in which R(2) is CHO, and the other radicals are as defined above, in any stereoisomeric form or mixture thereof in any ratio, or a physiologically tolerable salt thereof.

Preferred compounds of formula (I) are furthermore those in which X is O, and the other radicals are as defined above, in any stereoisomeric form or mixture thereof in any ratio, or a physiologically tolerable salt thereof.

Particularly preferred compounds of formula (I) are:

4-chloro-5-formyl-2-phenyl-1-[[4-[2-(n-butyloxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(n-butyloxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(n-propyloxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(ethoxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(methoxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(n-butylaminocarbonylsulfonamido)-5-isobutyl-3-thienyl]phenyl]methyl]imidazole, or a physiologically tolerable salt thereof;

5-formyl-4-methoxy-2-phenyl-1-[[4-[2-(ethylaminocarbonylsulfonamino)-5-isobutyl-3-thienyl]phenyl]methyl]imidazole, or a physiologically tolerable salt thereof;

5-formyl-4-methoxy-2-phenyl-1-[[4-[2-(methylaminocarbonylsulfonamido)-5-isobuty-3-thienyl]phenyl]methyl]imidazole, or a physiologically tolerable salt thereof;

5-formyl-4-methoxyethoxy-2-phenyl-1-[[4-[2-(n-butyloxycarbonylsulfonamido)-5-isobutyl-3-thienyl]phenyl]methyl]imidazole, or a physiologically tolerable salt thereof;

5-formyl-4-methoxy-2-phenyl-1-[[4-[2-(n-butyloxycarbonylsulfonamido)-5-isobutyl-3-thienyl]-2-chlorophenyl]methyl]imidazole, or a physiologically tolerable salt thereof;

5-formyl-4-methoxy-2-phenyl-1-[[4-[2-(n-butyloxycarbofnylsulfonamido)-5-isobutyl-3-thienyl]-2-chlorophenyl]methyl]imidazole, or a physiologically tolerable salt thereof;

4-chloro-5-formyl-2-phenyl-1-[[4-[2-(n-butyloxycarbonylsulfonamido)-5-n-propyl-3-thienyl]phenyl]methyl]imidazole, or a physiologically tolerable salt thereof;

5-formylmethoxy-2-phenyl-1-[[4-[2-(n-butyloxycarbonylsulfonamido)-5-n-propyl-3-thienyl]phenyl]methyl]imidazole, or a physiologically tolerable salt thereof;

5-formyl-4-methoxy-2-phenyl-1-[[4-[2-(methoxycarbonylsulfonamido)-5-n-propyl-3-thienyl]phenyl]methyl]imidazole, or a physiologically tolerable salt thereof;

5-formyl-4-methoxy-2phenyl-1-[[4-[2-(n-butylaminocarbonylsulfonamido)-5-n-propyl-3-thienyl]phenyl]methyl]imidazole, or a physiologically tolerable salt thereof;

5-formyl-4-methoxy-2-phenyl-1-[[4-[2-(methylaminocarbonylsulfonamido)-5-n-propyl-3-thienyl]phenyl]methyl]imidazole, or a physiologically tolerable salt thereof;

5-formyl-4-methoxy-2-phenyl-1-[[4-[2-(ethylaminocarbonylsulfonamido)-5-isobutyl-3-thienyl]phenyl]methyl]imidazole sodium salt;

5-formyl-4-methoxy-2-phenyl-1-[[4-[2-(ethylaminocarbonylsulfonamido)-5-isobutyl-3-thienyl]phenyl]methyl]imidazole L-lysine salt; or 5-formyl-4-methoxy-2-phenyl-1-[[4-[2-(ethylaminocarbonylsulfonamido)-5-isobutyl-3-thienyl]phenyl]methyl]imidazole tris(hydroxymethyl)aminomethane salt.

The invention furthermore relates to processes for the preparation of compounds of formula (I), comprising the following reaction:

a) Providing 4-chloro-5-formylimidazole derivatives of formula (III),

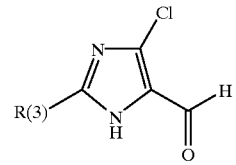

(III)

in which R(3) has the abovementioned meaning and whose preparation is described, for example, in *Chem. Pharm. Bull.* 24 (1976) 960–969, and reacting with p-bromobenzyl bromides of formula (IV),

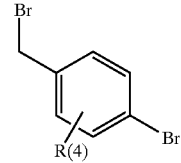

(IV)

in which R(4) is as defined above, resulting in the formation of compounds of formula (V)

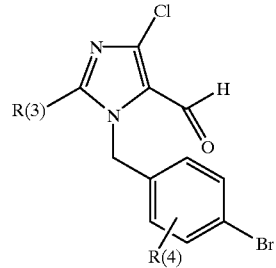

(V)

in which R(3) and R(4) have the abovementioned meanings, where the alkylation can be carried out in the presence of an organic or inorganic base such as, for example, triethylamine, $K_2CO_3$, or $Cs_2CO_3$ in an inert solvent such as, for example, DMF. Compounds of formula (IV) are commercially obtainable or can be prepared by methods known per se.

b) Compounds of formula (V) can be reacted with thiophene-3-boronic acids of formula (VI)

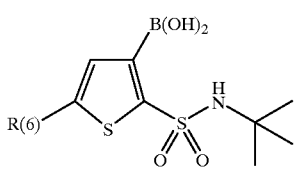

(VI)

in which R(6) is as defined above and whose preparation is disclosed in EP-A 512 675, to give 1-(p-thienyl) imidazoles of formula (VII)

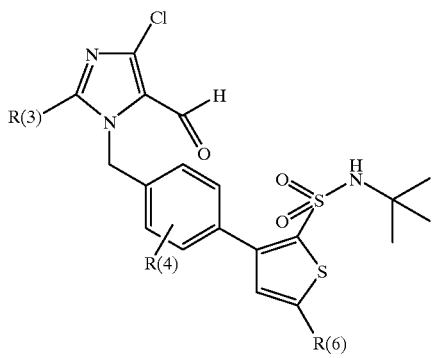

(VII)

in which R(3), R(4), and R(6) are as defined above. This Suzuki-type cross-coupling reaction is preferably carried out using palladium(II) acetate and triphenylphosphine or tetrakistriphenyjphosphinepalladium as catalysts in the presence of a base such as, for example, cesium or potassium carbonate, for example, in solvent mixtures of ethanol and toluene at temperatures up to the boiling point of the solvents; corresponding reactions are described, for example, in *Synthetic Commun.* 11 (1981) 513, *J. Med. Chem.* 38 (1995) 2357–2377, and *Liebigs Ann.* (1995) 1253–1257.

c) Compounds of formula (VII) can be converted by removal of the tert-butyl protective group into sulfonamides of formula (VIII)

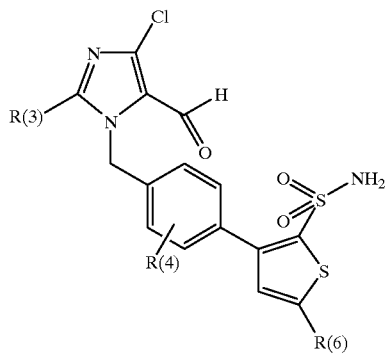

(VIII)

in which R(3), R(4), and R(6) are as defined above.

This removal is preferably carried out by treatment of compounds of formula (VII) with organic acids such as, for example, concentrated trifluoroacetic acid in the presence of anisole.

d) Compounds of formula (VIII) can be converted by substitution of the chlorine atorm in position 4 of the imidazole ring into compounds of formula (IX)

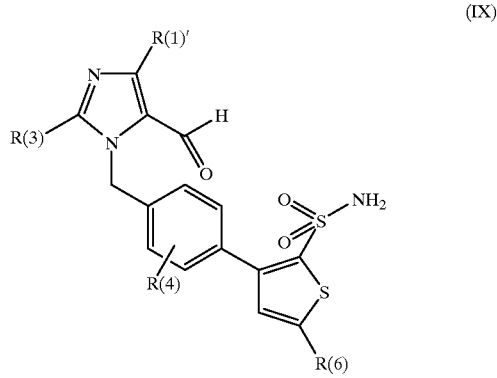

(IX)

in which R(3), R(4), and R(6) are as defined above, and R(1)' represents the radicals mentioned under (2) to (8) for R(1). This substitution of the chlorine atom can be carried out in this case, for example, by treatment of compounds of formula (VIII) with alkoxides formed in situ by the action of bases such as NaOH or NaH on the alcohols generally used as solvents, such as, for example, methanol, ethanol, or ethylene glycol monomethyl ether, at temperatures of from 50° C. up to the boiling point of the alcohols.

Alternatively, compounds of formula (IX) in which R(1)' is ($C_1$–$C_4$)-alkoxy can be converted via an ether cleavage, by treatment preferably of the methoxy ethers of formula (IX) with concentrated acids such as HI and HBr, or with Lewis acids such as $BF_3$, $BCl_3$, $BBr_3$, $AlCl_3$, or their etherates, preferably with $BBr_3$, in an inert solvent such as, for example, $CH_2Cl_2$, into the corresponding phenols, which can then be reacted by processes known per se with the suitably substituted halides such as, for example, 2-bromoethyl methyl ether or benzyl bromide in the presence of a base in an inert solvent at temperatures up to the boiling point of the solvent.

The corresponding diphenyl ether compounds can be obtained from the reaction of the phenols of formula (IX) with boronic acids such as, for example, phenylboronic acid or 4-methoxyphenylboronic acid in the presence of copper catalysts such as, for example, Cu(OAc)$_2$. Appropriate reactions are described, for example, in *Tetrahedron Lett.* 39 (1998) 2937–2940.

e) From sulfonamides of formula (IX), it is possible by reaction with R(5)-substituted chloroformic acid esters to prepare sulfonylurethanes of formula (Ia)

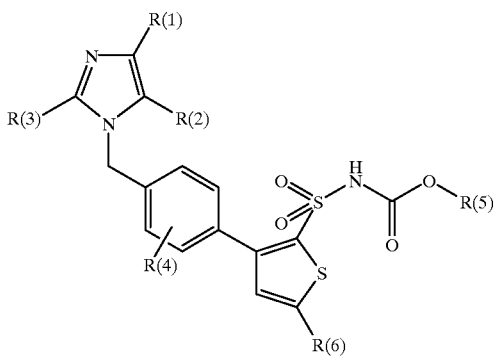

(Ia)

in which R(1), R(2), R(3), R(4), and R(6) are as defined above, and R(5) only has the meaning mentioned under (2) and (3). This reaction can be carried out in the presence of a base such as, for example, pyridine, and of an acylation accelerator, such as 4-pyrrolidinopyridine, at temperatures from room temperature (RT) to 150° C., but preferably at RT.

f) From sulfonamides of formula (IX), it is possible by treatment with R(5)-substituted isocyanates or isothiocyanates to obtain sulfonylureas of formula (Ib)

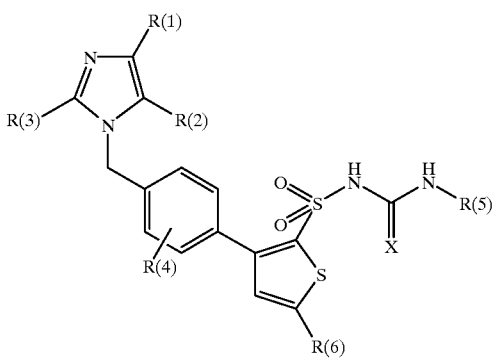

(Ib)

in which R(1), R(2), R(3), R(4), R(6), and X are as defined above, and R(5) only has the meaning mentioned under (2) and (3). The reaction with R(5)-substituted isocyanates and isothiocyanates can be carried out in the presence of a base in an inert solvent at temperatures from RT to 150° C.

Suitable bases are, for example, alkali metal or alkaline earth metal hydroxides, hydrides, amides, or alkoxides, such as sodium hydroxide, potassium hydroxide, calcium hydroxide, sodium hydride, potassium hydride, calcium hydride, sodium amide, potassium amide, sodium methoxide, sodium ethoxide, or potassium tert-butoxide. Suitable inert solvents are ethers such as THF, dioxane, ethylene glycol dimethyl ether, or diglyme, ketones such as acetone or butanone, nitrites such as acetonitrile, nitro compounds such as nitromethane, esters such as ethyl acetate, amides such as DMF or N-methylpyrrolidone, hexamethylphosphoramide, sulfoxides such as DMSO, and hydrocarbons such as benzene, toluene, or xylenes. Furthermore, mixtures of these solvents with one another are also suitable.

Sulfonylureas of formula (Ib) may also be prepared by reaction of amines R(5)-NH$_2$ with sulfonyl isocyanate derivatives that result from sulfonamides of formula (IX), for example, by treatment with phosgene or a phosgene substitute such as triphosgene.

Alternatively, sulfonylureas of formula (Ib) can be prepared by reaction of sulfonamides of formula (IX) with 2,2,2-trichloroacetamide derivatives of a suitable amine R(5)-NH$_2$ in the presence of a base in an inert, high-boiling solvent such as, for example, DMSO or from the corresponding sulfonylurethane of formula (Ia) accessible by reaction with ethyl chloroformate by action of the corresponding amine R(5)-NH$_2$ in an inert, high-boiling solvent such as, for example, toluene, at temperatures up to the boiling point of the respective solvent, which is described, for example, in *J. Med. Chem.* 38 (1995) 2357–2377, and in *Bioorg. Med. Chem.* 5 (1997) 673–678.

N-Unsubstituted sulfonylureas of formula (Ib), in which R(5) is hydrogen, can be prepared by hydrolysis of sulfonamidonitriles resulting after reaction of sulfonamides of formula (IX) with cyanogen bromide in the presence of K$_2$CO$_3$ in acetonitrile with sulfuric acid at temperatures of from −10° C. to 0° C.

By methods known per se, such as are described in the literature (e.g., in the standard works such as Houben-Weyl, *Methoden der Oranischen Chemie* (Methods of Organic Chemistry), Georg Thieme Verlag, Stuttgart; *Organic Reactions*, John Wiley & Sons, Inc., New York; or Larock, *Comprehensive Organic Transformations*, VCH, Weinheim), it is possible by oxidation of the aldehyde group in compounds of formula (I) to prepare the corresponding carboxylic acids or carboxylic acid esters of formula (I).

The invention also relates to compounds of formula (X)

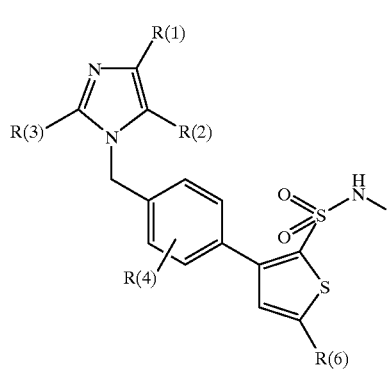

(X)

in which R is hydrogen or a suitable protective group such as, for example, (C$_1$–C$_6$)-alkyl, preferably tert-butyl, and the radicals R(1), R(2), R(3), R(4), and R(6) are as defined above, in any stereoisomeric form or mixture thereof in any ratio, or a physiologically tolerable salt thereof.

Compounds of formula (X) are valuable intermediates for the preparation of compounds of formula (I) according to the invention. In addition, compounds of formula (X) have a high affinity for the angiotensin (1–7) receptor and can be used as angiotensin (1–7) receptor agonists and thus as pharmaceuticals for the treatment and/or prophylaxis of illnesses which are primarily or secondarily caused or at least partly caused by a reduced production and/or release of the vasorelaxant, anti-thrombotic, and cardioprotective messengers cyclic 3',5'-guanosine monophosphate (cGMP) and nitrogen monoxide (NO). For example, these compounds are used for the treatment and/or prophylaxis of high blood pressure, cardiac hypertrophy, cardiac insufficiency, coronary heart diseases such as angina pectoris, cardiac infarct, vascular restenosis after angioplasty, cardiomyopathies, an endothelial dysfunction or. endothelial damage, e.g., as a result of arteriosclerotic processes or in diabetes mellitus, and also of arterial and venous thrombosis.

The vascular endothelium is a metabolically active organ with a large number of regulatory functions, that is capable of the synthesis and release of vasoactive substances. A dysfunction of the endothelial layer lining the vessel is correlated with the pathogenesis of various cardiovascular disorders such as arteriosclerosis and hypertension (*Eur. J. Clin. Invest.* 23 (1993) 670–685). An endothelial dysfunction is characterized by a reduced synthesis and/or release of the vasorelaxant, vasoprotective, antithrombotically, and antiproliferatively active messengers NO and cGMP, which play an important role in the prevention and regression of vascular remodeling and arterial hypertension. Substances that are able to stimulate the synthesis and release of these messengers are therefore valuable pharmaceuticals for the treatment of all diseases that are characterized by endothelial dysfunction.

A large number of published experiments confirm that a degradation product of therenin-angiotensin system, the heptapeptide angiotensin (1–7), is a potent, endogenous effector hormone of the renin-angiotensin system (Hypertension 12 (Suppl. III) (1991) III-126-III-133), whose biological action is caused by the stimulation of specific receptors, which preferably bind angiotensin (1–7) (Peptides 14 (1993) 679–684; Hypertension 29 (part 2) (1997) 388–393). This action is in many cases directed against that of the vasoconstrictory hormone angiotensin II or opposes this in a counter regulatory manner (Hypertension 30 (part 2) (1997) 535–541; Regulatory Peptides 78 (1998) 13–18).

Hypertension 19 (Suppl. II) (1992) II-49-II-55, and *Am. J. Cardiol.* 82 (1998) 17S–19S, showed that angiotensin (1–7) stimulated the production and/or the release of NO/cGMP and the prostaglandins $E_2$ and $I_2$, which is not blocked by pretreatment with $AT_1$ and $AT_2$ receptor antagonists.

An endothelium-dependent relaxation of intact coronary arteries of dogs and pigs was described in Hypertension 27 (part 2) (1996) 523–528, and an endothelium-dependent relaxation of intact, KCl-precontracted rat aortas by angiotensin (1–7), which is not affected by $AT_1$ receptor antagonists, was described in *J. Cardiovasc. Phermacol.* 30 (1997) 676–682.

The hypotensive action of angiotensin (1–7) in spontaneously hypertensive rats on continuous infusion by means of an osmotic minipump was shown in Peptides 14 (1993) 679–684, and in *Am. J. Physiol.* 269 (1995) H313-H319, angiotensin (1–7) in normotensive rats having no action on the blood pressure in the same dose. Complementary to these investigations, it was demonstrated in Hypettension 31 (1998) 699–705, that the infusion of an angiotensin (1–7) antibody increases the mean arterial blood pressure in conscious, spontaneously hypertensive rats which had been pretreated with lisinopril and losartan.

*Am. J. Hypertension* 11 (1998) 137–146, showed that in persons having essential hypertension, markedly lower plasma levels of angiotensin (1–7) are detectable than in normotensive persons.

The anti-proliferative action of angiotensin (1–7) on vascular smooth muscle cells was confirmed in Hypertension 28 (1996) 104–108, and the inhibition of the proliferation of smooth muscle cells after vascular tissue damage was confirmed in Hypertension 33 (part II) (1999) 207–211.

Moreover, angiotensin (1–7) in sodium chloride-loaded, anesthetized normotensive Wistar rats also showed renal effects such as increased natriuresis and diuresis (*Am. J. Physiol.* 270 (1996) F141-F147).

Compounds of formula (I) described here are potent, nonpeptide agonists of the postulated angiotensin (1–7) receptors, which are preferably located in the vessels (including endothelium), in the kidney, in the CNS, and in the heart. They therefore mimic the biological action of the peptide hormone angiotensin (1–7) directed against angiotensin II, described above, which is to be attributed to the production and/or release of cGMP and NO from the endothelium, without in this case being subject to the rapid metabolic degradation of this hormone. Because of the stimulation of the production and/or release of these vasorelaxant, antithrombotic, and cardioprotective messengers, angiotensin (1–7) receptor agonists of formula (I) described are valuable pharmaceuticals for the treatment and/or prophylaxis of illnesses which are primarily or secondarily caused, or at least partly caused, by a reduced production and/or release of the vasorelaxant, antithrombotic, and cardioprotective messengers cGMP and NO. These compounds can thus be employed, for example, in the treatment and/or prophylaxis of high blood pressure, cardiac hypertrophy, cardiac insufficiency, coronary heart diseases such as angina pectoris, cardiac infarct, vascular restenosis after angioplasty, cardiomyopathies, an endothelial dysfunction or endothelial damage, e.g., as a result of arteriosclerotic processes or in diabetes mellitus, and also of arterial and venous thrombosis.

The stimulation of endothelial angiotensin (1–7) receptors by agonists of formula (I) causes the release of vasodilatory and organ-protective autacoids. This mechanism differs here from that of ACE inhibition and $AT_1$ receptor blockade by the avoidance either of lowered tissue angiotensin II (in the case of ACE inhibitors) or of effects which still cannot be estimated at present, which are associated with increased ANG II plasma values (in the case of $AT_1$ receptor antagonists).

Compounds of formula (I) or their physiologically tolerable salts can thus be used in animals, preferably in mammals, and in particular in humans, as pharmaceuticals either on their own, as mixtures with one another or together with other active compounds, in particular in the form of pharmaceutical preparations. The present invention therefore relates to the use of compounds of formula (I) and/or their physiologically tolerable salts for the production of a medicament for the therapy or prophylaxis of the above-mentioned syndromes, and to pharmaceutical preparations which contain an efficacious dose of at least one compound of formula (I) and/or of a physiologically tolerable salt thereof as active constituent in addition to at least one customary, pharmaceutically innocuous vehicle and/or excipient. The pharmaceutical preparations can be intended for enteral or parenteral use, and normally contain 0.5 to 90% by weight of at least one compound of formula (I) and/or a physiologically tolerable salt thereof. The amount of active compound of formula (I) and/or a physiologically tolerable salt thereof in the pharmaceutical preparations is in general 0.2 to 500 mg, preferably 1 to 300 mg.

Pharmaceuticals employed according to the invention, which contain at least one compound of formula (I), and/or a physiologically tolerable salt thereof, can be administered enterally, for example orally or rectally, in the form of pills, tablets, film-coated tablets, sugar-coated tablets, granules, hard and soft gelatin capsules, solutions such as aqueous, alcoholic, or oily solutions, juices, drops, syrups, emulsions, or suspensions. Administration can also be carried out parenterally, for example subcutaneously, intramuscularly, or intravenously in the form of injection solutions or infusion solutions. Further possible administration forms are, for example, percutaneous or topical administration, in the form of ointments, creams, pastes, lotions, gels, sprays, powders, foams, aerosols, or solutions, or use in the form of implants.

The pharmaceutical preparations employed according to the invention can be prepared by the known standard processes for the production of pharmaceutical preparations. For this, at least one compound of formula (I) and/or a physiologically tolerable salt thereof are brought together with at least one solid or liquid pharmaceutical vehicle and/or additive or excipient, and, if desired, in combination with at least one other pharmaceutical active compound having therapeutic or prophylactic action, for example cardiovascular-active pharmaceuticals such as, for example, calcium antagonists, ACE inhibitors, $AT_1$ receptor antagonists, NO donors, endothelin receptor antagonists, $K^+$ channel openers, phosphodiesterase inhibitors, diuretics, or α- and β-blockers, into a suitable administration form or dose form, which can then be used as a pharmaceutical in human medicine or veterinary medicine.

Possible vehicles are organic or inorganic substances which are suitable for enteral (for example oral) or parenteral (for example intravenous) administration or topical application and do not react with active compounds of formula (I), for example water, vegetable oils, alcohols such as ethanol, isopropanol, or benzyl alcohol, 1,2-propanediol, polyethylene glycols, glycerol triacetate, gelatin, carbohydrates such as lactose or starch, magnesium stearate, talc, lanolin, petroleum jelly, acetonitrile, dimethylformamide, and dimethylacetamide. In particular, pharmaceutical forms such as tablets, sugar-coated tablets, capsules, solutions, preferably oily or aqueous solutions, syrups, juices, or drops. Furthermore, suspensions or emulsions are used for oral and rectal administration. Mixtures of two or more vehicles can also be employed, for example, mixtures of two or more solvents, in particular also mixtures of at least one organic solvent with water. As additives or excipients, the pharmaceutical preparations can contain, for example, stabilizing and/or wetting agents, emulsifiers, salts, for example for affecting the osmotic pressure, lubricants, preservatives, colorants and flavorings, and/or aromatizers and buffer substances. If desired, they can also contain at least one further active compound, for example at least one vitamin. Compounds of formula (I) and/or their physiologically tolerable salts can also be lyophilized and the lyophilizates obtained can be used, for example, for the production of injection preparations. Liposomal preparations are also particularly suitable for topical application.

The dose of at least one active compound of formula (I) to be administered and/or of a physiologically tolerable salt thereof in the case of use according to the invention depends on the individual case and is to be tailored to the individual conditions as customary for an optimal action. Thus it depends on the nature and severifty of the illness to be treated, and on the sex, age, weight, and individual responsiveness of the human or animal to be treated, on the potency and duration of action of the compounds employed, on whether the therapy is acute or chronic or prophylaxis is carried out, or on whether further active compounds are administered in addition to compounds of formula (I). In general, a dose range for the treatment of the abovementioned syndromes in humans of approximately 0.1 mg to approximately 100 mg per kg per day on administration to an adult weighing about 75 kg is adequate to achieve the desired action. A dose range of 1 to 20 mg per kg per day (in each case mg per kg of body weight) is preferred. The daily dose can be administered here as an individual dose or can be divided into a number, for example, 1, 2, 3, or 4, of individual doses. It can also be administered continuously. If appropriate, depending upon individual behavior, it may be necessary to deviate upwards or downwards from the daily dose indicated. Pharmaceutical preparations normally contain 0.2 to 500 mg, preferably 1 to 300 mg, of at least one active compound of formula (I) and/or a physiologically tolerable salt thereof.

The invention also very generally comprises the use of preferably nonpeptide compounds which bring about a stimulation of angiotensin (1–7) receptors which are located, for example, in the vessels (including endothelium), in the kidney, in the CNS, and in the heart, as pharmaceuticals, preferably for oral administration, or for use as substances which stimulate the production and/or release of the vasorelaxant, antithrombotic, and cardioprotective messengers cGMP and NO, and as pharmaceuticals for the treatment and/or prophylaxis of illnesses which are primarily or secondarily caused or at least partly caused by a reduced production and/or release of the vasorelaxant, antithrombotic, and cardioprotective messengers cGMP and NO, in particular for the treatment and prophylaxis of high blood pressure, cardiac hypertrophy, cardiac insufficiency, coronary heart diseases such as angina pectoris, cardiac infarct, vascular restenosis after angioplasty, cardiomyopathies, an endothelial dysfunction or endothelial damage, e.g., as a result of arteriosclerotic processes or in diabetes mellitus, and also of arterial and venous thrombosis.

List of abbreviations:

| | |
|---|---|
| abs. | absolute |
| cGMP | cyclic 3',5'-guanosine monophosphate |
| $CH_2Cl_2$ | dichloromethane |
| DCI | desorption chemical ionization |

| | |
|---|---|
| DMF | N,N-dimethylformamide |
| EA | ethyl acetate |
| ESI | electron spray ionization |
| FAB | fast atom bombardment |
| M.p. | melting point |
| satd | saturated |
| h | hour(s) |
| min | minute(s) |
| NO | nitrogen monoxide |
| RT | room temperature |
| THF | tetrahydrofuran |

The invention is illustrated by the examples below, without being restricted to these.

EXAMPLES

Example 1

4-Chloro-5-formyl-2-phenyl-1-[[4-[2-(n-butyloxycarbonylsulfonamido)-5-isobutyl-3-thienyl]phenyl]methyl]imidazole

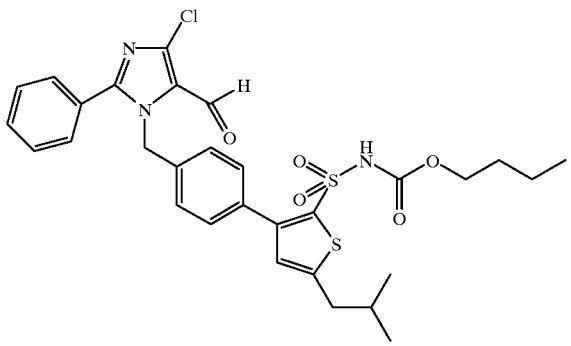

a) 4-Chloro-1-[(4-bromophenyl)methyl]-5-formyl-2-phenylimidazole

A solution of 8.0 g (32.0 mmol) of 4-chloro-5-formyl-2-phenylimidazole (prepared according to *Chem. Pharm. Bull.* 24 (1976) 960–969) and 5.3 g (32.0 mmol) of $K_2CO_3$ in 200 ml of abs. DMF was stirred at RT for 20 min. A solution of 9.6 g (32.0 mmol) of 4-bromobenzyl bromide in 200 ml of abs. DMF was then added dropwise and the reaction solution was stirred at RT for 6 h. It was concentrated in vacuo, and the residue obtained was taken up in EA, washed with water, 10% strength $KHSO_4$, 10% strength $NaHCO_3$, and satd sodium chloride solution, and dried over $Na_2SO_4$. Chromatographic purification on $SiO_2$ using EA/heptane (1:4) as eluent of the residue which remained after stripping off the EA yielded 11.5 g of the title compound in the form of a beige solid.

M.p.: 92–95° C. $R_f(SiO_2$, EA/heptane 1:4)=0.24 MS (ESI): m/e=375/377 $[M+H]^+$ b) 4-Chloro-5-formyl-2-phenyl-1-[[4-[2-(N-tert-butylsulfonamido)-5-isobutyl-3-thienyl]phenyl]methyl]imidazole A solution of 7.2 g (22.6 mmol) of 5-isobutyl-2-[(N-tert-butyl)sulfonamido]-thiophene-3-boronic acid (disclosed in EP-A 512 675) in 125 ml of ethanol was added dropwise at RT to a solution of 8.5 g (22.6 mmol) of the compound from Example 1a) and 800 mg of tetrakistriphenylphosphinepalladium(0) in 100 ml of toluene. 26 ml of a 2 M $Cs_2CO_3$ solution were added and the resultant reaction solution was stirred at reflux for 5 h. It was concentrated to dryness and the residue that remained was taken up in EA/water (1:1). The organic phase was separated off, washed with water, dried over $Na_2SO_4$, and concentrated. Chromatographic purification of the residue on $SiO_2$ using EA/heptane (1:4) as eluent afforded 6.7 g of the title compound as a white solid.

M.p.: 104–105° C. $R_f(SiO_2$, EA/heptane 1:2)=0.26 MS (ESI): m/e=570 $[M+H]^+$ c) 4-Chloro-5-formyl-2-phenyl-1-[[4-[2-sulfonamido-5-isobutyl-3-thienyl]phenyl]-methyl]imidazole A solution of 3.3 g (5.96 mmol) of the compound from Example 1b) and 3.5 ml (5.96 mmol) of anisole in 33 ml of trifluoroacetic acid was stirred at RT for 48 h. It was concentrated to dryness in vacuo and the residue was taken up in EA. The EA solution was washed with water, dried over $Na_2SO_4$, and concentrated. After chromatographic purification of the residue on $SiO_2$ using EA/heptane (1:1) as eluent, 1.52 g of the desired compound was obtained, in the form of a slowly crystallizing solid.

M.p.: 118–120° C. $R_f(SiO_2$, EA/heptane 1:1)=0.32 MS (ESI): m/e=515 $[M+H]^+$ d) 4-Chloro-5-formyl-2-phenyl-1-[[4-[2-(n-butyloxycarbonylsulfonamido)-5-isobutyl-3-thienyl]phenyl]methyl]imidazole A solution of 100 mg (0.19 mmol) of the compound from Example 1c) in 1.7 ml of abs. pyridine was treated successively with 3 mg (0.02 mmol) of 4-pyrrolidinopyridine and 252 µl (0.19 mmol) of butyl chloroformate in an argon atmosphere. The reaction solution was stirred at RT for 24 h. 0.7 ml of methanol were then added, the solution was concentrated to dryness, and the residue was taken up in EA. The EA solution was then washed with a 10% strength citric acid solution, water, and a satd sodium chloride solution, dried over $Na_2SO_4$, and concentrated. Chromatographic purification on $SiO_2$ using EA/heptane (1:1) of the residue obtained after stripping off the solvent finally yielded 85 mg of the title compound in the form of an amorphous solid.

$R_f(SiO_2$, EA/heptane 1:1)=0.15 MS (FAB): m/e=614 $[M+H]^+$

Example 2

5-Formyl-4-methoxy-2-phenyl-1-[[4-[2-(n-butyloxycarbonylsulfonamido)-5-isobutyl-3-thienyl]phenyl]methyl]imidazole

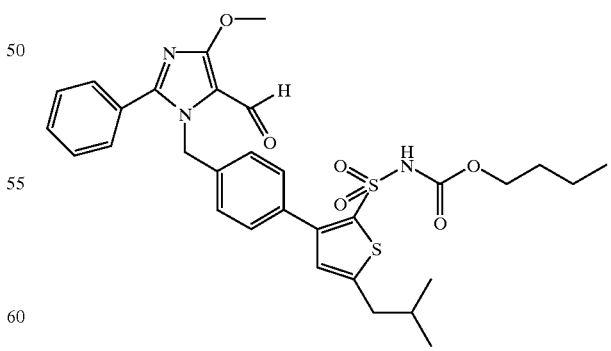

a) 5-Formyl-4-methoxy-2-phenyl-1-[[4-[2-sulfonamido-5-isobutyl-3-thienyl]-phenyl]methyl]imidazole A solution of 850 mg (1.65 mmol) of the compound from Example 1c) in 25 ml of methanol was treated with 665 mg (16.53 mmol) of NaOH and stirred under reflux for 20 h. The reaction solution was concentrated, the residue was taken up in 60 ml EA/water (1:1), the pH of the solution was adjusted to 6 by addition of 1 N hydrochloric acid, and the organic phase was separated off. The aqueous phase was extracted twice with EA and the combined organic phases were dried over $Na_2SO_4$. Chromatographic. purification on $SiO_2$ using EA/heptane (1:1) as eluent of the residue obtained after stripping off the EA afforded 690 mg of the title compound in the form of a yellow, amorphous foam.

$R_f(SiO_2$, EA/heptane 1:1)=0.23 MS (FAB): m/e=510 $[M+H]^+$ b) 5-Formyl-4-methoxy-2-phenyl-1-[[4-[2-(n-butyloxycarbonylsulfonamido)-5-isobutyl-3-thienyl]phenyl]methyl]imidazole The title compound was prepared by reaction of the compound from Example 2a) with butyl chloroformate according to the process mentioned in Example 1d). In this case, starting from 106 mg (0.21 mmol) of the compound from Example 2a) after chromatographic purification on $SiO_2$ using EA/heptane (1:1) as eluent, 75 mg of the desired compound was obtained as an amorphous foam.

$R_f(SiO_2$, EA/heptane 1:1)=0.18 MS (ESI): m/e=610 $[M+H]^+$

Example 3

5-Formyl-4-methoxy-2-phenyl-1-[[4-[2-(n-propyloxycarbonylsulfonamido)-5-isobutyl-3-thienyl]phenyl]methyl]imidazole

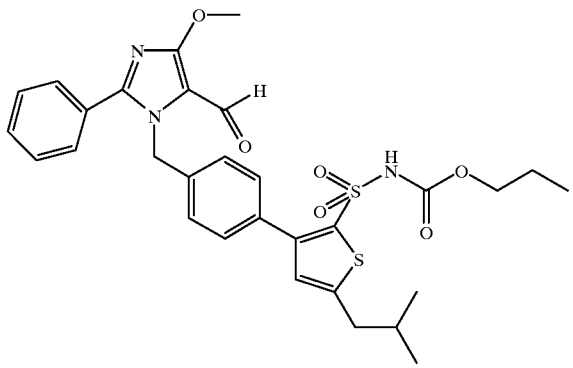

The title compound was prepared by reaction of the compound from Example 2a) with propyl chloroformate according to the process mentioned in Example 1d). In this case, starting from 60 mg (0.12 mmol) of the compound from Example 2a) after chromatographic purification on $SiO_2$ using EA/heptane (1:1) as eluent, 61 mg of the title compound were obtained as an amorphous foam.

$R_f(SiO_2$, EA/heptane 1:1)=0.13 MS (ESI): m/e=596 $[M+H]^+$

Example 4

5-Formyl-4-methoxy-2-phenyl-1-[[4-[2-(ethoxycarbonylsulfonamido)-5-isobutyl-3-thienyl]phenyl]methyl]imidazole

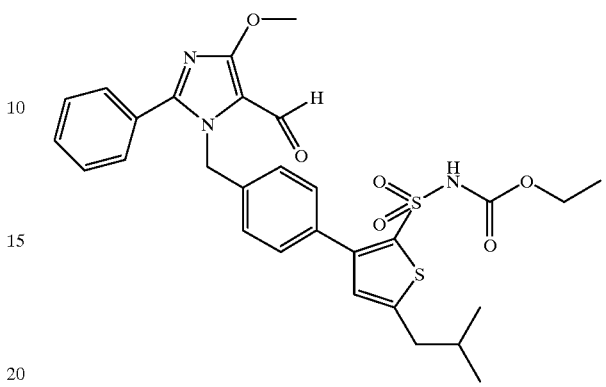

The title compound was prepared by reaction of the compound from Example 2a) with ethyl chloroformate according to the process mentioned in Example 1d). In this case, starting from 60 mg (0.12 mmol) of the compound from Example 2a) after chromatographic purification on $SiO_2$ using EA/heptane (1:1) as eluent, 55 mg of the title compound were obtained as an amorphous foam.

$R_f(SiO_2$, EA/heptane 1:1)=0.10 MS (ESI): m/e=582 $[M+H]^+$

Example 5

5-Formyl-4-methoxy-2-phenyl-1-[[4-[2-(methoxycarbonylsulfonamido)-5-isobutyl-3-thienyl]phenyl]methyl]imidazole

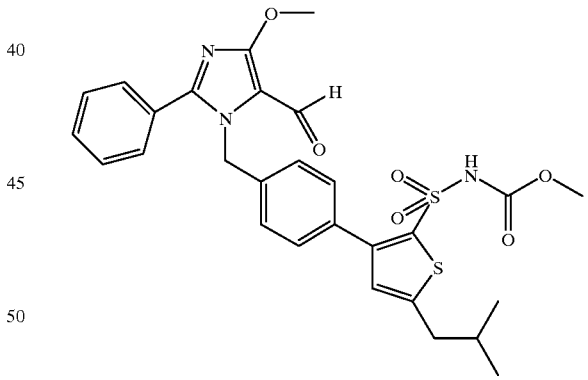

A solution of 80 mg (0.16 mmol) of the compound from Example 2a), 43.3 mg (0.32 mmol) of $K_2CO_3$, and 8.3 mg of dimethylaminopyridine in 6 ml of diethylene glycol dimethyl ether was treated with 16.8 μl (0.16 mmol) of dimethyl dicarbonate and then stirred under reflux for 1.5 h. The reaction solution was concentrated to dryness arid the residue was taken up in a solution of EA and a 10% strength $KH_2PO_4$ solution (1:1). The organic phase was separated off, washed twice with a 10% strength $KH_2PO_4$ solution, dried over $Na_2SO_4$, and concentrated. Chromatographic purification of the residue on $SiO_2$ using EA/heptane (2:1) as eluent, yielded 55 mg of the title compound in the form of an amorphous foam.

R_f(SiO_2, EA/heptane 4:1)=0.23 MS (ESI): m/e=568 [M+H]+

Example 6

5-Formyl-4-methoxy-2-phenyl-1-[[4-[2-(n-butylaminocarbonylsulfonamido)-5-isobutyl-3-thienyl]phenyl]methyl]imidazole

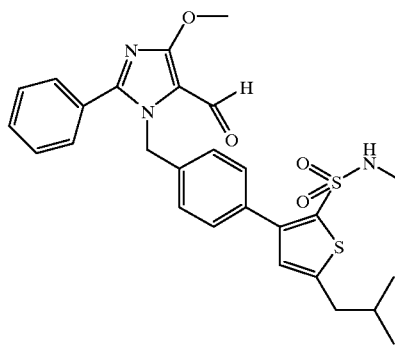

A solution of 60 mg (0.12 mmol) of the compound from Example 2a) in 2 ml of abs. DMF was treated successively with 48 mg (0.35 mmol) of K_2CO_3 and 13.2 μl (0.12 mmol) of n-butyl isocyanate and then stirred under reflux for 3 h. After cooling, 15 ml of a 10% strength KH_2PO_4 solution were added to the reaction solution and the solution obtained was extracted a number of times with EA. The combined organic phases were dried over Na_2SO_4 and concentrated. The residue obtained was treated with EA/diisopropyl ether and the precipitate deposited was filtered off with suction. Drying of the precipitate in vacua afforded 55 mg of the title compound.

M.p.: 131–133° C.

R_f(SiO_2, EA/heptane 4:1)=0.30 MS (FAB): m/e=609 [M+H]+

Example 7

5-Formyl-4-methoxy-2-phenyl-1-[[4-[2-(ethylaminocarbonylsulfonamido)-5-isobutyl-3-thienyl]phenyl]methyl]imidazole

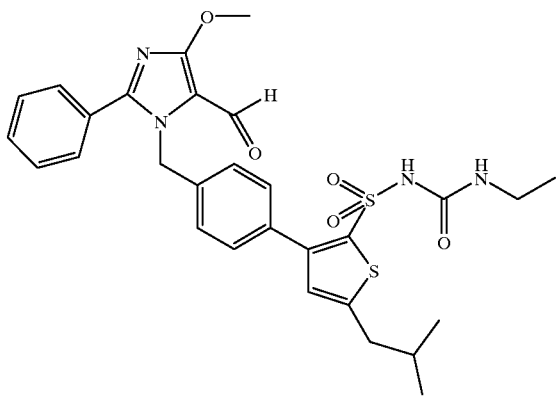

The title compound was prepared by reaction of the compound from Example 2a) with ethyl isocyanate according to the process mentioned in Example 6). In this case, starting from 60 mg (0.12 mmol) of the compound from Example 2a), 46 mg of the title compound were obtained.

M.p.: 105–106° C. R_f(SiO_2, EA/heptane 4:1)=0.30 MS (ESI): m/e=581 [M+H]+

Example 8

5-Formyl-4-methoxy-2-phenyl-1-[[4-[2-(methylaminocarbonyisulfonamido)-5-isobutyl-3-thienyl]phenyl]methyl]imidazole

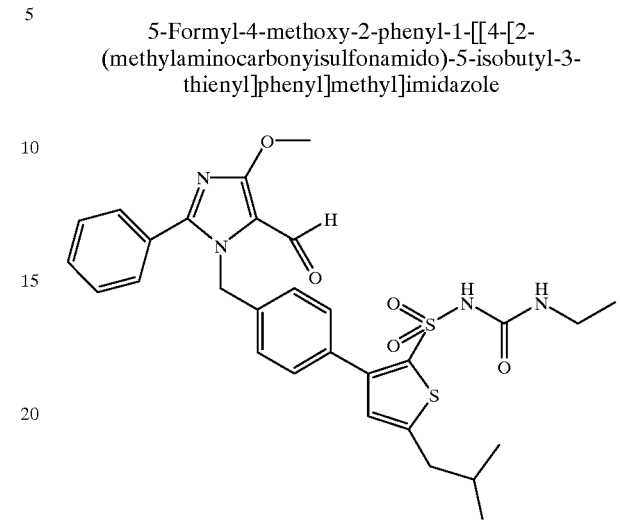

A solution of 80 mg (0.16 mmol) of the compound from Example 2a) in 1.5 ml of DMSO was treated with 30.4 mg (0.17 mmol) of N-methyl-2,2,2-trichloroacetamide and 19.1 mg (0.47 mmol) of powdered NaOH and stirred at 80° C. for 1h. The reaction solution was cooled, treated with ice, and the pH was adjusted to 4 by addition of 2 N hydrochloric acid. The precipitate that deposited in the course of this was filtered off with suction, washed with water, dried, and purified by chromatography on SiO_2 using EA/heptane (2:1) as eluent. 62 mg of the title compound were obtained in the form of a white solid.

M.p.: 102–103° C.

R_f(SiO_2, EA/heptane 4:1)=0.14 MS (ESI): m/e 567 [M+H]+

Example 9

5-Formyl-4-methoxyethoxy-2-phenyl-1-[[4-[2-(n-butyloxycarbonylsulfonamido)-5-isobutyl-3-thienyl]phenyl]methyl]imidazole

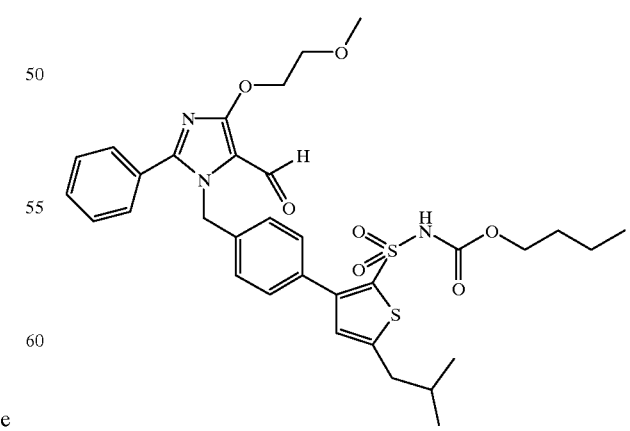

a) 5-Formyl-4-methoxyethoxy-2-phenyl-1-[[4-[2-sulfonamido-5-isobutyl-3-thienyl]phenyl]methyl]imidazole A solution of 200 mg (0.38 mmol) of the compound from Example 1c) in 7.8 ml of ethylene glycol monomethyl ether was treated with 155 mg (3.89 mmol) of powdered NaOH in an argon atmosphere and then stirred at 80° C. for 5 h. It was concentrated to dryness and the residue obtained was taken up in a saturated NaHCO$_3$ solution and EA. The EA phase was separated off and the aqueous solution was extracted several times with EA. The organic phases were combined, dried over Na$_2$SO$_4$, and concentrated. Chromatographic purification on SiO$_2$ using EA/heptane (1:1) of the remaining residue yielded 140 mg of the title compound as a pale yellow-colored solid.

M.p.: 91–92° C. R$_f$(SiO$_2$, EA/heptane 1:1)=0.12 MS (FAB): m/e=554 [M+H]$^+$ b) 5-Formyl-4-methoxyethoxy-2-phenyl-1-[[4-[2-(n-butyloxycarbonylsulfonamido)-5-isobutyl-3-thienyl]phenyl]methyl]imidazole The title compound was prepared by reaction of the compound from Example 9a) with butyl chloroformate according to the process mentioned in Example 1d). In this case, starting from 70 mg (0.13 mmol) of the compound from Example 9a) after chromatographic purification on SiO$_2$ using EA/heptane (1:1) as eluent, 78 mg of the title compound was obtained as an amorphous foam.

R$_f$(SiO$_2$, EA/heptane 1:1)=0.07 MS (ESI): m/e=654 [M+H]$^+$

Example 10

5-Formyl-4-methoxy-2-phenyl-1-[[4-[2-(n-butyloxycarbonylsulfonamido)-5-isobutyl-3-thienyl]-2-chlorophenyl]methyl]imidazole

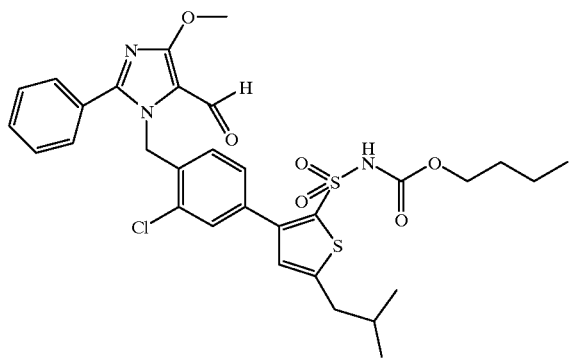

a) 4-Chloro-1-[(4-bromo-2-chlorophenyl)methyl]-5-formyl-2-phenyl-imidazole

The title compound was prepared by reaction of 4-chloro-5-formyl-2-phenylimidazole with 4-bromo-2-chlorobenzyl bromide according to the process mentioned in Example 1a). In this case, starting from 2.0 g (9.68 mmol) of 4-chloro-5-formyl-2-phenylimidazole, 2.6 g of the title compound was obtained.

R$_f$(SiO$_2$, EA/heptane 1:2)=0.56 MS (DCI): m/e=409/411 [M+H]$^+$ b) 4-Chloro-5-formyl-2-phenyl-1-[[4-[2-(N-tert-butylsulfonamido)-5-isobutyl-3-thienyl]-2-chlorophenyl]methyl]imidazole The title compound was prepared by reaction of the compound from Example 10a) and 5-isobutyl-2-[(N-teit-butyl)sulfonamido]thiophene-3-boronic acid according to the process mentioned in Example 1b). In this case, starting from 2.0 g (4.88 mmol) of the compound from Example 10a), 1.2 g of the title compound were obtained in the form of a pale brown oil.

R$_f$(SiO$_2$, EA/heptane 1:2)=0.47 MS (FAB): m/e=604 [M+H]$^+$ c) 4-Chloro-5-formyl-2-phenyl-1-[[4-[2-sulfonamido-5-isobutyl-3-thienyl]-2-chlorophenyl]methyl]imidazole The title compound was prepared from the compound from Example 10b) according to the process mentioned in Example 1c). Starting from 1.2 g (1.99 mmol) of the compound from Example 10b), 606 mg of the title compound was obtained as an amorphous, yellow foam.

R$_f$(SiO$_2$, EA/heptane 1:2)=0.32 MS (FAB): m/e=548 [M+H]$^+$ d) 5-Formyl-2-methoxy-2-phenyl-1-[[4-[2-sulfonamido-5-isobutyl-3-thienyl]-2-chlorophenyl]methyl]imidazole The title compound was prepared from the compound from Example 10c) according to the process mentioned in Example 2a). In this case, starting from 400 mg (0.73 mmol) of the compound from Example 10c), 280 mg of the title compound was obtained in the form of a yellow, amorphous foam.

M.p.: 60° C. (softening) R$_f$(SiO$_2$, EA/heptane 1:2)=0.20 MS (ESI): m/e=544 [M+H]$^+$ e) 5-Formyl-4-methoxy-2-phenyl-1-[[4-[2-(n-butyloxycarbonylsulfonamido)-5-isobutyl-3-thienyl]-2-chlorophenyl]methyl]imidazole The title compound was obtained from the reaction of the compound from Example 10d) with butyl chloroformate according to the process mentioned in Exarrple 1d). Starting from 200 mg (0.37 mmol) of the compound from Example 10d), 167 rrg of the desired compound were obtained in the form of a beige solid.

M.p.: 58° C. (softening) R$_f$(SiO$_2$, EA/heptane 1:1)=0.45 MS (ESI): m/e=644 [M+H]$^+$ Example 11

5-Formyl-4-methoxy-2-phenyl-1-[[4-[2-(n-butyloxycarbonylsulfonamido)-5-isobutyl-3-thienyl]-2-chlorophenyl]methyl]imidazole

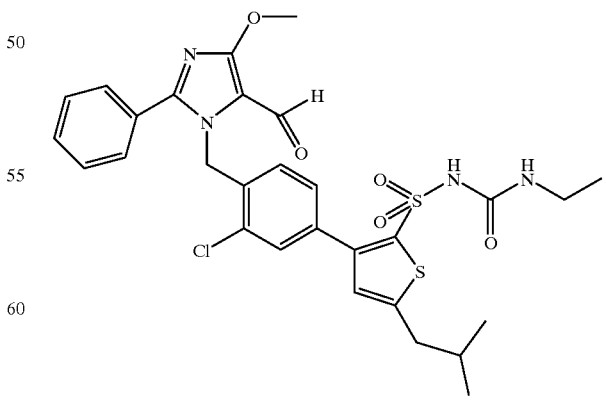

The title compound was obtained from the reaction of the compound from Example 10d) with ethyl isocyanate according to the process described in Example 7). In this case, starting from 74 mg (0.14 mmol) of the compound from Example 10d) after chromatographic purification on SiO$_2$ using CH$_2$Cl$_2$/methanol (20:1) as eluent, 35 mg of the title compound was obtained in the form of a white solid.

M.p.: 83° C. (softening) R$_f$(SiO$_2$, EA/heptane 1:1)=0.30 MS (ESI): m/e=614 [M+H]$^+$ Example 12

4-Chloro-5-formyl-2-phenyl-1-[[4-[2-(n-butyloxycarbonylsulfonamido)-5-n-propyl-3-thienyl]phenyl]methyl]imidazole

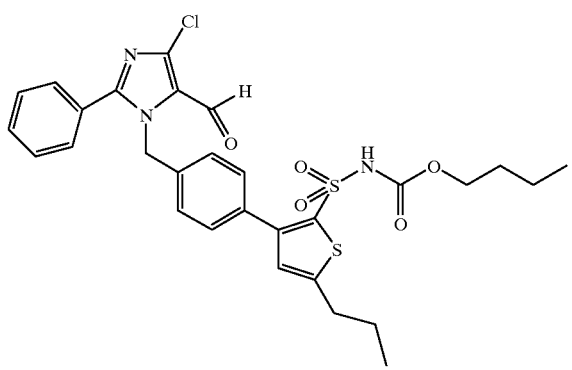

a) 4-Chloro-5-formyl-2-phenyl-1-[[4-[2-(N-teft-butylsulfonamido)-5-n-propyl-3-thienyl]phenyl]methyl]imidazole The title compound was prepared by the reaction of the compound from Example 1a) with 5-n-propyl-2-[(N-tert-butyl)sulfonamido]thiophene-3-boronic acid (disclosed in EP-A 512 675) according to the process mentioned in Example 1b). In this case, starting from 4.8 g (13.1 mmol) of the compound from Example 1a) after chromatographic purification on SiO$_2$ using EA/heptane (1:3) as eluent, 2.9 g of the title compound were obtained in the form of a white solid.

M.p.: 140° C. R$_f$(SiO$_2$, EA/heptane 1:2)=0.30 MS (FAB): m/e=556 [M+H]$^+$ b) 4-Chloro-5-formyl-2-phenyl-1-[[4-[2-sulfonamido-5-n-propyl-3-thienyl]phenyl]methyl]imidazole The title compound was prepared from the compound from Example 12a) according to the process mentioned in Example 1c). Starting from 1.9 g (3.56 mmol) of the compound from Example 12a), after chromatographic purification on SiO$_2$ using EA/heptane (1:2) as eluent, 1.1 9 of the title compound was obtained as a white solid.

M.p.: 93–95° C. R$_f$(SiO$_2$, EA/heptane 1:2)=0.18 MS (ESI): m/e=500 [M+H]$^+$ c) 4-Chloro-5-formyl-2-phenyl-1-[[4-[2-(n-butyloxycarbonylsulfonamido)-5-n-proyl-3-thienyl]phenyl]methyl]imidazole The title compound was prepared by reaction of the compound from Example 12b) with butyl chloroformate according to the process mentioned in Example 1d). In this case, starting from 100 mg (0.20 mmol) of the compound from Example 12b), after chromatographic purification on SiO$_2$ using EAheptane (1:1) as eluent, 90 mg of the title compound were obtained.

R$_f$(SiO$_2$, EA/heptane 1:1)=0.14 MS (ESI): m/e=600 [M+H]$^+$

Example 13

5-Formyl-4-methoxy-2-phenyl-1-[[4-[2-(n-butyloxycarbonylsulfonamido)-5-n-propyl-3-thienyl]phenyl]methyl]imidazole

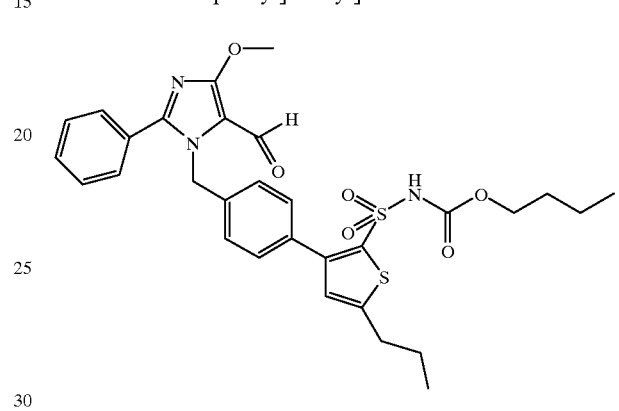

a) 5-Formyl-4-methoxy-2-phenyl-1-[[4-[2-sulfonamido-5-n-propyl-3-thienyl]phenyl]methyl]imidazole The title compound was prepared by reaction of the compound from Example 12b) according to the process mentioned in Example 2a). In this case, starting from 850 mg (1.70 mmol) of the compound from Example 12b), after chromatographic purification on SiO$_2$ using EA/heptane (1:2) as eluent, 460 mg of the title compound was obtained in the form of a white solid.

M.p.: 85–86° C. R$_f$(SiO$_2$, EA/heptane 1:1)=0.22 MS (ESI): m/e=496 [M+H]$^+$ b) 5-Formyl-4-methoxy-2-phenyl-1-[[4-[2-(n-butyloxycarbonylsulfonamido)-5-n-propyl-3-thienyl]phenyl]methyl]imidazole The title compound was prepared by reaction of the compound from Example 13a) with butyl chloroformate according to the process mentioned in Example 1d). In this case, starting from 60 mg (0.12 mmol) of the compound from Example 13a), after chromatographic purification on SiO$_2$ using EA/heptane (1:1) as eluent, 52 mg of the title compound were obtained.

R$_f$(SiO$_2$, EA/heptane 1:1)=0.18 MS (ESI): m/e=596 [M+H]$^+$

Example 14

5-Formyl-4-methoxy-2-phenyl-1-[[4-[2-(methoxycarbonylsulfonamido)-5-n-propyl-3-thienyl]phenyl]methyl]imidazole

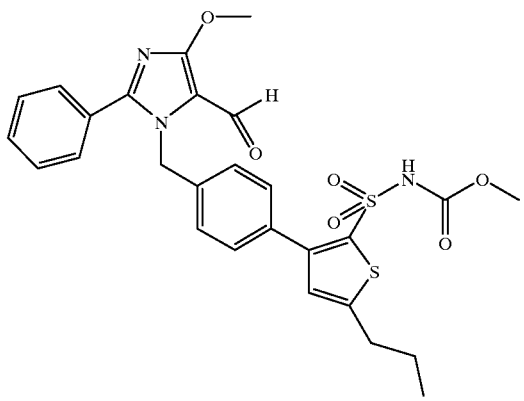

The title compound was prepared by reaction of the compound from Example 13b) with dimethyl dicarbonate according to the process mentioned in Example 5). Starting from 75 mg (0.15 mmol) of the compound from Example 13b), after chromatography on SiO$_2$ using EA/heptane (2:1) as eluent, 66 mg of the title compound were obtained as an amorphous solid.

R$_f$(SiO$_2$, EA/heptane 4:1)=0.18 MS (ESI): m/e=554 [M+H]$^+$

Example 15

5-Formyl-4-methoxy-2-phenyl-1-[[4-[2-(n-butylaminocarbonylsulfonamido)-5-n-propyl-3-thienyl]phenyl]methyl]imidazole

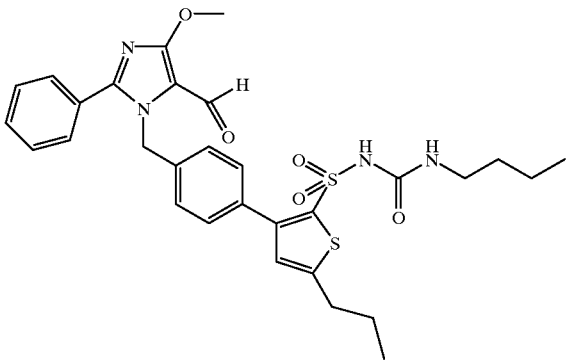

The title compound was prepared by reaction of the compound from Example 13b) with n-butyl isocyanate according to the process mentioned in Example 6). Starting from 59 mg (0.12 mmol) of the compound from Example 13b), after chromatography on SiO$_2$ using EA/heptane (1:1) as eluent, 54 mg of the title compound were obtained as an amorphous solid.

R$_f$(SiO$_2$, EA/heptane 4:1)=0.25 MS (ESI): m/e=595 [M+H]$^+$

Example 16

5-Formyl-4-methoxy-2-phenyl-1-[[4-(2-(methylaminocarbonylsulfonamido)-5-n-propyl-3-thienyl]phenyl]methyl]imidazole

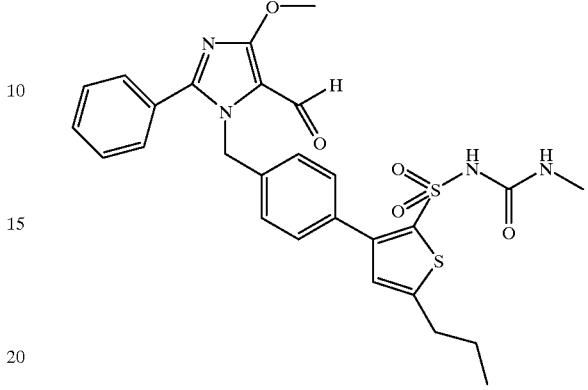

The title compound was prepared by reaction of the compound from Example 13b) with N-methyl-2,2,2-trichloroacetamide according to the process mentioned in Example 8). Starting from 70 mg (0.14 mmol) of the compound from Example 13b), after chromatography on SiO$_2$ using EA/heptane (2:1) as eluent, 55 mg of the title compound were obtained as an amorphous solid.

R$_f$(SiO$_2$, EA/heptane 4:1)=0.15 MS (ESI): m/e=553 [M+H]$^+$

Example 17

5-Formyl-4-methoxy-2-phenyl-1-[[4-[2-(ethylaminocarbonylsulfonamido)-5-isobutyl-3-thienyl]phenyl]methyl]imidazole sodium salt 220 mg (0.38 mmol) of the compound from Example 7 were treated with 3.7 ml of a freshly prepared 0.1 molar sodium methoxide solution and the resulting solution was stirred at RT for 1 h. The reaction solution was concentrated to dryness and the residue obtained was dissolved in 4 ml of n-butyl acetate with slight warming. The precipitate crystallizing out after storage in a refrigerator for 3 days was filtered off with suction and washed with a little cold n-butyl acetate. Drying under high vacuum finally yielded 120 mg of the desired sodium salt.

M.p.: 170° C. MS (ESI): m/e=603 [M+H]$^+$

Example 18

5-Formyl-4-methoxy-2-phenyl-1-[[4-[2-(ethylaminocarbonylsulfonamido)-5-isobutyl-3-thienyl]phenyl]methyl]imidazole L-lysine salt

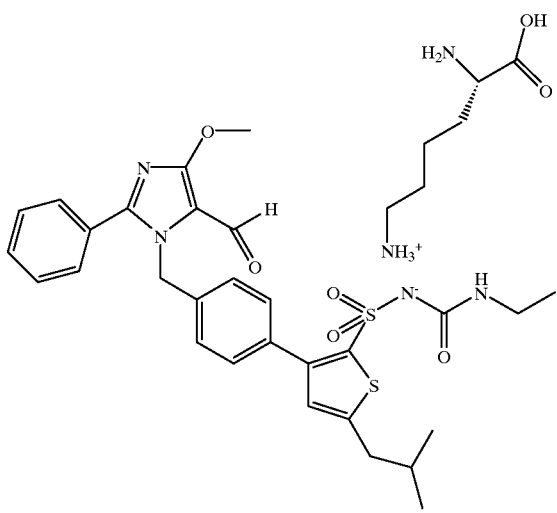

A solution of 500 mg (0.86 mmol) of the compound from Example 7 and 125.8 mg (0.86 mmol) of L-lysine in 100 ml of ethanol and 25 ml of water was stirred at RT for 2 h. It was then concentrated to dryness, the residue was taken up in 30 ml of water, and the solution obtained was freeze-dried. 200 mg of the amorphous residue several days, the precipitate that crystallized out was filtered off and dried under high vacuum. 68 mg of the title compound was obtained as pale yellow-colored crystals.

M.p.: 180° C. MS (ESI): m/e=727 [M+H]$^+$

Example 19

5-Formyl-4-methoxy-2-phenyl-1-[[4-[2-(ethylaminocarbonylsulfonamido)-5-isobutyl-3-thienyl]phenyl]methyl]imidazole tris(hydroxymethyl)aminomethane salt

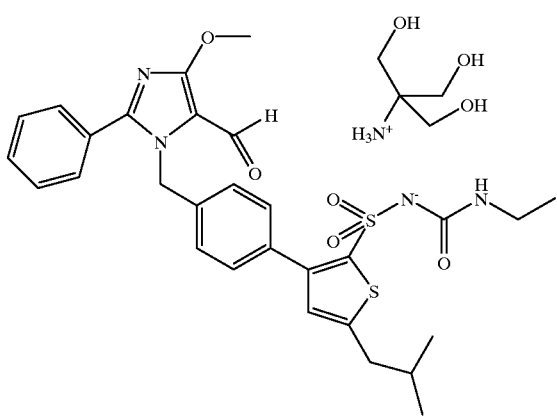

A solution of 300 mg (0.516 mmol) of the compound from Example 7 and 62.6 mg (0.516 mmol) of tris(hydroxymethyl)aminomethane in 75 ml of ethanol and 15 ml of water was stirred at RT for 2 h. It was then concentrated to dryness, the residue was taken up in water, and the solution obtained was freeze-dried. The amorphous residue obtained was dissolved with heating in 30 ml n-butyl acetate. After storage in a refrigerator for several days, the precipitate that crystallized out was filtered off and dried under high vacuum. 120 mg of the title compound was obtained as pale yellow-colored crystals. M.p.: 144–145° C. MS (ESI): m/e=702 [M+H]$^+$ The affinity of compounds of formula (I) for angiotensin (1–7) binding sites, and their agonistic properties on endothelial cells, were demonstrated in the following assays (tests 1 and 2):

Test 1: Binding assay

The affinity of compounds of formula (I) for angiotensin (1–7) receptors was measured by ligand displacement experiments on membrane preparations of primary bovine aorta endothelial cells, such as are also described, for example, in Hypertension 29 (part 2) (1997) 388–393.

a) Membrane preparation:

Following obtainment of endothelial cells from bovine aortas (test 1, a), the cells were cultured in 75 cm$^2$ culture bottles (Becton Dickinson, Heidelberg) until achieving confluence. The cells were then taken up with ice-cold phosphate/NaCl/EDTA buffer (50 mmol/l NaHPO$_4$, 0.15 mol/l NaCl, 5 mmol/l EDTA, pH 7.2), detached with a rubber scraper, and centrifuged (1500×g, 5 min). The resulting cell pellet was frozen (−80° C.) for later membrane preparation. The thawed cell pellet was homogenized (glass/Teflon Potter, 1000 rpm, 10 strokes) in ice-cold phosphate/NaCl/EDTA buffer. Membrane isolation was carried out by subsequent centrifugation (30,000×g, 20 min) of the cell homogenate. The cell pellet thus obtained was resuspended in modified HEPES buffer (10 nmol/l HEPES, 0.1 mol/l NaCl, 5 mmol/l MgCl$_2$, pH 7.4) with addition of 0.2% bovine serum albumin and a protease inhibitor cocktail (COMPLETE®, Boehringer Mannheim). After subsequent protein determination (according to Lowry) of the membrane suspension, this was used immediately for the ligand binding test.

b) Binding experiments:

The tests were carried out on 96-well opaque plates that are equipped with Durapore filters (0.65 μm pore size; Millipore, Eschborn). Before the beginning of the test, the filters were pretreated with 1% bovine serum albumin for 30 min in order to minimize the nonspecific binding of the radioactive ligand and of the cold substances to the filter material. The incubation was carried out in a total volume of 200 μl: 50 μl of $^{125}$I-ANG (1–7), 20 μl of cold, nonradioactive ANG (1–7) or test substances of formula (I), 30 μl of buffer, and 100 μl of membranes (20 μg of protein). The binding reaction was started by addition of the radioactive ligand. The incubation of the samples was carried out with continuous shaking at RT for 45 min. The binding reaction was ended by means of vacuum filtration (−20 kPa vacuum; multiscreen filtration system, Millipore, Eschborn). In order to completely remove the non-membrane-bound, free radioactivity, the filters were washed in vacuo twice with 250 μl of ice-cold phosphate/NaCl/EDTA buffer (50 mmol/l of NaHPO$_4$, 0.15 mol/l of NaCl, 5 mmol/l of EDTA, pH 7.2), and then dried. The radioactive content on the dried filters was determined by means of a gamma counter.

For the competition experiments (determination of "individual values" or IC$_{50}$ values), a concentration of 7.5 to 10 nmol/l of $^{125}$I-ANG (1–7) (specific activity 1500–2100 mCi/mg) was employed, with and without increasing concentrations of the test substances of formula (I). The nonspecific binding was in each case measured in the presence of 10 μmol/l of nonradioactive ANG (1–7).

c) Results:

| Example | IC$_{50}$ (nM) |
|---|---|
| 2a | 20 |
| 2b | 30 |
| 4 | 5 |
| 7 | 20 |

The results confirm the high affinity of compounds of formula (I) for the angiotensin (1–7) receptor on endothelial cells.

With respect to ANGII receptors of the AT$_1$ and AT$_2$ type, compounds of formula (I) in this case have no or only negligible (>10$^{-6}$ M) affinity.

Test 2: Functional assay

As a marker of the production and release of NO in endothelial cells, the stimulating action of compounds of formula (I) on the production of intracellular cGMAP was measured on primary-cultured endothelial cells of bovine aortas, such as is described, for example, in *J. Pharmacol. Exp. Ther.* 262 (1992) 729–733.

a) Cell cultures:

After enzymatic digestion (Dispase II; Boehringer, Mannheim) of the endothelial cells from the bovine aorta, the endothelial cells were taken up in culture medium (Dulbecco's modified Eagle's Ham's F 12 Medium 1:1 with penicillin (10 U/l), streptomycin (10 µg/l), L-glutamine (1 mmol/l), gtutathione, and L-(+)-ascorbic acid (in each case 5 mg/l) and heat-inactivated fetal calf serum (20%)), washed once (centrifugation at 170×g, 10 min), and resuspended in culture medium. The cell suspension thus obtained was inoculated (~250 µg of protein or 3×10$^{-5}$ cells per well) into 6-well plates (Nunc Intermed, Wiesbaden), made up with culture medium, and kept at 37° C. in an incubator which was humidified and aerated with 95% O$_2$/5% CO$_2$.

b) cGMP determinations:

After reaching confluence (6–8 days after inoculation), the culture medium was removed and the cell monolayer was washed twice with warm HEPES/Tyrode's solution. The cells were then pre-incubated for 15 min at 37° C. in HEPES/Tyrode's solution which contains IBMX (3-isobutyl-1-methylxanthine, 10$^{-4}$ mol/l, Serva, Heidelberg). The incubation was started by addition of SOD (superoxide dismutase from bovine erythrocytes, 3×10$^{-7}$mol/l, Serva, Heidelberg) and the test substances of formula (I) in the given concentrations. After the appropriate incubation time, the incubation medium was aspirated, and the remaining cells were immediately extracted into 1 N formic acid-acetone (v/v, 15:85) and scraped off. The suspension obtained was ultrasonicated (10 sec) and then centrifuged off (3000×g, 10 min). For the determination of cGMP by means of radioimmunoassay (New England Nuclear, Boston, Mass.), the supernatant was lyophilized and taken up in sodium acetate buffer (0.05 mol/l; pH 6.2). The content (pmol) of intracellular cGMP was related to mg of cell protein.

c) Results:

| Example | EC$_{50}$ (µM) |
|---|---|
| 2a | 0.5 |
| 2b | 0.3 |
| 4 | 0.1 |
| 7 | 0.5 |

The results confirm the agonistic action of compounds of formula (I) on angiotensin (1–7) receptors.

The action of the compound according to the invention on the production of cGMP as a marker of the NO synthesis and release is not affected here by preincubation with an angiotensin II receptor antagonist either of the AT$_1$ subtype such as EXP3174, or of the AT$_2$ subtype such as PD 123,319. In contrast to this, the described stimulating effect of the compound according to the invention on the cGMP is inhibited by preincubation with a selective antagonist of angiotensin (1–7) receptors, [D-Ala$^7$]-angiotensin (1–7), which is described, for example, in *Brain Res. Bull.* 35 (1994) 293–298, which confirms the specificity of this functional effect.

The action of compounds of formula (I) on the heart was demonstrated in the model of isolated, working rat hearts (test 3) which is described, for example, in *J. Cardiovasc. Pharmacol.* 8 (Suppl. 10) (1986) S91–S99.

Test 3: Isolated, working rat hearts a) Method:

Isolated hearts of Wistar-Kyoto rats (280–300 g body weight) are perfused with a constant perfusion pressure of 60 mmHg according to the method of Langendorff using an oxygen-saturated (95% O$_2$, 5% CO$_2$), nonrecirculating, modified Krebs-Henseleit buffer solution (118 mmol/l of NaCl, 4.7 mmol/l of KCl, 2.5 mmol/l of CaCl$_2$, 1.6 mmol/l of MgSO$_4$, 24.9 mmol/l of NaHCO$_3$, 1.2 mmol/l of KH$_2$PO$_4$, 5.5 mmol/l of glucose, and 2.0 mmol/l of sodium pyruvate). For the measurement of the coronary flow, a catheter having an electromagnetic measuring head placed in the pulmonary artery was used. After a 15-minute equilibration period, the heart is converted into the working mode, in which a preload of 15 mmHg and an afterload of 60 mmHg is set. The working load of the heart remains constant during the entire test time of 90 minutes. Flow and pressure signals for the analysis are recorded by means of a PLUG-SYS measuring system (Hugo Sachs Elektronik). The analysis of the data is carried out at a collection frequency of 500 Hz, averaged every 2 seconds, using the software Aquire Plus VI.21f (PO-NE-MAH).

b) Results:

On perfusion of the hearts (n=4) at a concentration of 10$^{-6}$ mol/l of the compound from Example 2, the following values for the coronary flow were determined in comparison to control hearts (n=4):

| 1. Treated hearts: | |
|---|---|
| Coronary flow (ml/min) | Time (min) |
| 8.92 ± 0.68 | 0 |
| 11.29 ± 0.90 | 5 |
| 12.17 ± 0.74 | 10 |
| 12.22 ± 0.10 | 15 |

| 2. Control hearts: | |
|---|---|
| Coronary flow (ml/min) | Time (min) |
| 8.98 ± 0.59 | 0 |
| 8.94 ± 0.52 | 5 |
| 9.04 ± 0.70 | 10 |
| 8.91 ± 0.44 | 15 |

The heart rate remained unchanged in both groups during the entire experiment.

This significant increase in the coronary flow in isolated, working rat hearts confirms the cardioprotective action of compounds of formula (I).

The action of compounds of formula (I) on collagen-induced platelet aggregation was investigated in human platelet-rich plasma, which is described, for example, in G.V. Born et al., *Nature* (1962).

Test 4:

a) Method:

Human platelet-rich plasma (PRP) from 6 blood donors was incubated with the test compound at 37° C. for 20 min, then activated with collagen, and the maximal aggregation of the platelets was quantified in % via light transmission.

b) Result:

On incubation of the platelet-rich plasma with 30 µM of the compound from Example 2, the following values were determined for platelet aggregation (n=6):

Collagen (=maximal aggregation): 92±2.7% aggregation

Collagen+30 µM of the compound from Example 2: 52±5.7% aggregation

This significant inhibition of the platelet aggregation of human platelet-rich plasma confirms the antithrombotic action of compounds of formula (I).

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A compound of formula (X)

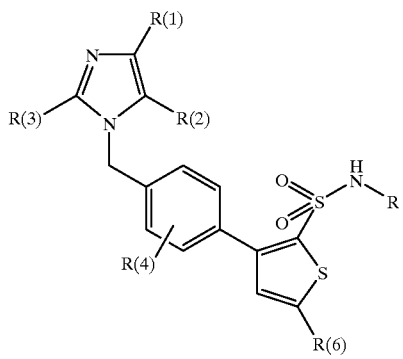

in which:

R is
   (1) hydrogen; or
   (2) $(C_1-C_6)$-alkyl;

R(1) is
   (1) halogen;
   (2) hydroxyl;
   (3) $(C_1-C_4)$-alkoxy;
   (4) $(C_1-C_8)$-alkoxy, wherein 1 to 6 carbon atoms are replaced by the heteroatoms O, S, or NH;
   (5) $(C_1-C_4)$-alkoxy, substituted by a saturated cyclic ether;
   (6) O—$(C_1-C_4)$-alkenyl;
   (7) O—$(C_1-C_4)$-alkylaryl; or
   (8) phenoxy, unsubstituted or substituted by a substituent selected from halogen, $(C_1-C_3)$-alkyl, $(C_1-C_3)$-alkoxy, and trifluoromethyl;

R(2) is
   (1) CHO;

R(3) is
   (1) $(C_1-C_4)$-alkyl; or
   (2) aryl;

R(4) is
   (1) hydrogen;
   (2) halogen; or
   (3) $(C_1-C_4)$-alkyl; and

R(6) is
   (1) $(C_1-C_5)$-alkyl;

in any stereoisomeric form or mixture thereof in any ratio, or a physiologically tolerable salt thereof.

2. A pharmaceutical composition, comprising at least one compound of claim 1, and at least one pharmaceutically tolerable carrier or excipient.

3. A pharmaceutical composition of claim 2, further comprising at least one other pharmaceutically active compound.

4. A method for treating or preventing illnesses which are primarily or secondarily caused or at least partly caused by reduced production and/or release of the vasorelaxant, antithrombotic, and cardioprotective messengers cyclic 3', 5'-guanosine monophosphate and nitrogen monoxide, comprising administering to a patient in need thereof an effective amount of at least one compound of claim 1.

5. A method for treating or preventing high blood pressure, cardiac hypertrophy, cardiac insufficiency, coronary heart diseases such as angina pectoris, cardiac infarct, vascular restenosis after angioplasty, cardiomyopathies, endothelial dysfunction or endothelial damage, and also of arterial and venous thromboses, comprising administering to a patient in need thereof an effective amount of at least one compound of claim 1.

* * * * *

UNITED STATES PATENT AND TRADEMARK OFFICE
CERTIFICATE OF CORRECTION

PATENT NO. : 6,429,222 B2
DATED : August 6, 2002
INVENTOR(S) : Heitsch et al.

It is certified that error appears in the above-identified patent and that said Letters Patent is hereby corrected as shown below:

<u>Title page,</u>
Insert -- [73] Assignee: Aventis Pharma Deutschland GmbH, Frankfurt am Main, Germany --.

Item [57], ABSTRACT,
Line 1, "1-(p-thienylbenzy)imidazoles" should read -- -1-(p-thienylbenzyl)imidazoles --.

Signed and Sealed this

Twelfth Day of November, 2002

*Attest:*

JAMES E. ROGAN
*Attesting Officer*   Director of the United States Patent and Trademark Office